US011603339B2

(12) United States Patent
Cruz et al.

(10) Patent No.: US 11,603,339 B2
(45) Date of Patent: *Mar. 14, 2023

(54) CHROMIUM-BASED CATALYSTS AND PROCESSES FOR CONVERTING ALKANES INTO HIGHER AND LOWER ALIPHATIC HYDROCARBONS

(71) Applicant: Chevron Phillips Chemical Company LP, The Woodlands, TX (US)

(72) Inventors: Carlos A. Cruz, Kingwood, TX (US); Max P. McDaniel, Bartlesville, OK (US); Masud M. Monwar, Bartlesville, OK (US); Jared Barr, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/847,303

(22) Filed: Jun. 23, 2022

(65) Prior Publication Data

US 2022/0324776 A1 Oct. 13, 2022

Related U.S. Application Data

(63) Continuation of application No. 17/013,912, filed on Sep. 8, 2020, now Pat. No. 11,396,485.

(60) Provisional application No. 62/900,683, filed on Sep. 16, 2019.

(51) Int. Cl.
| | | |
|---|---|---|
| *C07C 2/84* | (2006.01) | |
| *B01J 23/26* | (2006.01) | |
| *C07C 4/06* | (2006.01) | |
| *B01J 21/06* | (2006.01) | |
| *B01J 21/08* | (2006.01) | |
| *B01J 35/02* | (2006.01) | |
| *B01J 35/10* | (2006.01) | |
| *B01J 37/16* | (2006.01) | |
| *B01J 38/00* | (2006.01) | |

(52) U.S. Cl.
CPC .............. *C07C 2/84* (2013.01); *B01J 21/063* (2013.01); *B01J 21/08* (2013.01); *B01J 23/26* (2013.01); *B01J 35/023* (2013.01); *B01J 35/1019* (2013.01); *B01J 35/1023* (2013.01); *B01J 35/1038* (2013.01); *B01J 37/16* (2013.01); *B01J 38/00* (2013.01); *C07C 4/06* (2013.01); *C07C 2521/06* (2013.01); *C07C 2521/08* (2013.01); *C07C 2523/26* (2013.01)

(58) Field of Classification Search
CPC ......... C07C 2/84; C07C 4/06; C07C 2521/06; C07C 2521/08; C07C 2523/26; B01J 21/063; B01J 21/08; B01J 23/26; B01J 35/023; B01J 35/1019; B01J 35/1023; B01J 35/1038; B01J 37/16; B01J 38/00
See application file for complete search history.

(56) References Cited

U.S. PATENT DOCUMENTS

| | | | |
|---|---|---|---|
| 2,162,011 A * | 6/1939 | Guinot | C07C 5/3332 585/662 |
| 2,857,442 A | 10/1958 | Hay | |
| 3,166,537 A | 1/1965 | Gregg | |
| 3,201,476 A | 8/1965 | Baker | |
| 3,242,099 A | 3/1966 | Manyik | |
| 3,245,179 A | 4/1966 | Hawkins | |
| 3,857,901 A | 12/1974 | Dowden | |
| 3,887,494 A | 6/1975 | Dietz | |
| 4,248,735 A | 2/1981 | McDaniel | |
| 4,393,253 A | 7/1983 | Michaelson | |
| 4,501,885 A | 2/1985 | Sherk | |
| 4,588,790 A | 5/1986 | Jenkins, III | |
| 4,794,096 A | 12/1988 | Ewen | |
| 4,808,561 A | 2/1989 | Welborn, Jr. | |
| 5,220,080 A | 6/1993 | Lyons | |
| 5,352,749 A | 10/1994 | Dechellis | |
| 5,436,304 A | 7/1995 | Griffin | |
| 5,565,175 A | 10/1996 | Hottovy | |
| 5,575,979 A | 11/1996 | Hanson | |
| 5,576,259 A | 11/1996 | Hasegawa | |
| 5,641,842 A | 6/1997 | McDaniel | |
| 5,739,220 A | 4/1998 | Shamshoum | |
| 5,807,938 A | 9/1998 | Kaneko | |
| 5,919,983 A | 7/1999 | Rosen | |

(Continued)

FOREIGN PATENT DOCUMENTS

| | | |
|---|---|---|
| CN | 101264953 B | 8/2010 |
| CN | 106893015 B | 9/2019 |

(Continued)

OTHER PUBLICATIONS

International Search Report and Written Opinion, PCT/US2020/050655, dated Dec. 3, 2020, 16 pages.

(Continued)

*Primary Examiner* — Youngsul Jeong
*Assistant Examiner* — Jason Y Chong
(74) *Attorney, Agent, or Firm* — Merchant & Gould P.C.

(57) ABSTRACT

Processes for cracking an alkane reactant to form a lower aliphatic hydrocarbon product and for converting an alkane reactant into a higher aliphatic hydrocarbon product are disclosed, and these processes include a step of contacting the alkane reactant with a supported chromium (II) catalyst. In addition to the formation of various aliphatic hydrocarbons, such as linear alkanes, branched alkanes, 1-alkenes, and internal alkenes, aromatic hydrocarbons and hydrogen also can be produced.

20 Claims, No Drawings

(56) References Cited

U.S. PATENT DOCUMENTS

| | | |
|---|---|---|
| 6,239,235 B1 | 5/2001 | Hottovy |
| 6,262,191 B1 | 7/2001 | Hottovy |
| 6,825,377 B1 | 11/2004 | Beller |
| 6,833,415 B2 | 12/2004 | Kendrick |
| 7,112,643 B2 | 9/2006 | McDaniel |
| 7,238,756 B2 | 7/2007 | Ehrman |
| 7,294,599 B2 | 11/2007 | Jensen |
| 7,304,199 B2 | 12/2007 | Xu |
| 7,326,760 B2 | 2/2008 | Cann |
| 7,407,591 B2 | 8/2008 | De Battisti |
| 7,531,606 B2 | 5/2009 | Hendrickson |
| 7,598,327 B2 | 10/2009 | Shaw |
| 7,601,665 B2 | 10/2009 | McDaniel |
| 7,648,940 B2 | 1/2010 | Holtcamp |
| 7,649,062 B2 | 1/2010 | Matsunaga |
| 7,884,163 B2 | 2/2011 | McDaniel |
| 7,956,138 B2 | 6/2011 | Holtcamp |
| 8,114,353 B2 | 2/2012 | Benham |
| 8,114,946 B2 | 2/2012 | Yang |
| 8,309,485 B2 | 11/2012 | Yang |
| 8,623,973 B1 | 1/2014 | McDaniel |
| 8,703,886 B1 | 4/2014 | Yang |
| 8,822,608 B1 | 9/2014 | Bhandarkar |
| 8,969,228 B2 | 3/2015 | Nazarpoor |
| 9,006,367 B2 | 4/2015 | McDaniel |
| 9,023,959 B2 | 5/2015 | McDaniel |
| 9,096,699 B2 | 8/2015 | McDaniel |
| 9,169,337 B2 | 10/2015 | Rohatgi |
| 9,273,170 B2 | 3/2016 | Hlavinka |
| 9,346,897 B2 | 5/2016 | Cui |
| 9,394,393 B2 | 7/2016 | Hlavinka |
| 9,796,798 B2 | 10/2017 | Praetorius |
| 9,802,841 B2 | 10/2017 | Maruo |
| 9,988,468 B2 | 6/2018 | McDaniel |
| 10,000,594 B2 | 6/2018 | Hlavinka |
| 10,213,766 B2 | 2/2019 | Praetorius |
| 10,287,369 B2 | 5/2019 | Schwerdtfeger |
| 10,358,506 B2 | 7/2019 | Ding |
| 10,435,527 B2 | 10/2019 | Praetorius |
| 10,442,881 B2 | 10/2019 | Hlavinka |
| 10,654,953 B2 | 5/2020 | McDaniel |
| 2004/0059070 A1 | 3/2004 | Whitte |
| 2008/0032886 A1 | 2/2008 | Yeh |
| 2010/0274063 A1* | 10/2010 | Wang .................... C10G 11/05 585/324 |
| 2013/0072739 A1* | 3/2013 | Ruettinger ............ B01J 35/023 585/662 |
| 2014/0221692 A1 | 8/2014 | Netemeyer |
| 2017/0073439 A1 | 3/2017 | Ewart |
| 2017/0267607 A1 | 9/2017 | Choi |
| 2017/0274356 A1 | 9/2017 | Cann |
| 2018/0079845 A1 | 3/2018 | Doufas |
| 2019/0184389 A1 | 6/2019 | Neygandhi |
| 2019/0308172 A1 | 10/2019 | Zou |
| 2020/0086307 A1 | 3/2020 | Monwar |
| 2020/0087430 A1 | 3/2020 | Clear |

FOREIGN PATENT DOCUMENTS

| | | |
|---|---|---|
| CN | 108439533 B | 7/2020 |
| JP | 2012101986 A | 5/2012 |
| WO | 199011268 W | 10/1990 |
| WO | 2018125690 A1 | 7/2018 |
| WO | 2020060888 A2 | 3/2020 |
| WO | 2020060889 A2 | 3/2020 |

OTHER PUBLICATIONS

Awasthy, A.K. and Jan Rocek, "The Nature of the Transition State in the Oxidation of Olefins by Chromium (VI)," JACS 91;4, Feb. 12, 1969, pp. 991-996.

Baker, L. M., et al., Oxidation of olefins by supported chromium oxide, The Journal of Organic Chemistry, vol. 33, No. 2, pp. 616-618 (Year: 1968).

Barzan, et al., Ligands Make the Difference: Molecular Insights into CrVI/SiO2 Phillips Catalyst during Ethylene Polymerization, J. Am. Chem. Soc., 2017, 139, 47, 17064-17073.

Brown, et al., "Mechanism of Initiation in the Phillips Ethylene Polymerization Catalyst: Redox Processes Leading to the Active Site", ACS Catal. 2015, 5, 5574-5583.

Cainelli, et al., "Reactivity and Structure Concepts in Organic Chemistry", vol. 19, "Chromium Oxidations in Organic Chemistry", Springer Verlag Berlin 1984, p. 8.

Chakrabarti, et al., "Operando Molecular Spectroscopy During Ethylene Polymerization by Supported CrOx/SiO2 Catalysts: Active Sites,Reaction Intermediates, and Structure-Activity Relationship", Top. Catal. 2016, 59 p. 725-739.

Cruz, et al., "Identification of the Starting Group on the Initial PE Chain Produced by Phillips Catalyst", Macromolecules 2019, 52, 5750-5760.

Economy, et.al., "Supported Barium Chromate—A New Oxidation Catalyst", J. Catalysis, vol. 4, No. 4, Aug. 1, 1965, pp. 446-453.

Fendrick, et. al, "Actinacyclobutanes. Implementation of Thermochemically Based Strategies for the Ring-Opening Stoichiometric C—H Functionalization of Saturated and Olefinic Hydrocarbons", J. Am. Chem. Soc. 1986,108, 425-437.

Finch, "Reduction Studies on Supported Chromic Anhydride Catalysts," Journal of Catalysis, 43, 1976, pp. 111-121.

Floryan, et al., Strain Effect and Dual Initiation Pathway in Cr(III)/SiO2 Polymerization Catalysts from Amorphous Periodic Models, J Catalysis 2017, 346, 50-56.

Gierada, et. al., "Active sites formation and their transformations during ethylene polymerization by the Phillips CrOx/SiO2 catalyst", J. Catal., 2017, 352, 314-328.

Groppo, et al., "The Structure of Active Centers and the Ethylene Polymerization Mechanism on the Cr/SiO2 Catalyst: A Frontier for the Characterization Method", Chem. Rev. 2005, 105, 115-183.

International Search Report and Written Opinion for PCT/US2020/049680 dated Nov. 13, 2020. pp. 1-15.

International Search Report and Written Opinion, PCT/US2020/050650, dated Dec. 2, 2020, 14 pages.

International Search Report and Written Opinion, PCT/US2020/050657, dated Dec. 21, 2020, 15 pages.

Joseph, et al., "Products of the Initial Reduction of the Phillips Catalyst by Olefins", Journal of Catalysis 377 (2019) 550-564.

Kissin, et al., "Chemistry of Olefin Polymerization Reactions with Chromium-Based Catalysts", Journal of Polymer Science: Part A: Polymer Chemistry, 2008, 46, 5330-5347.

Kohler, et al., "Infrared Spectroscopic Characterization of Chromium Carbonyl Species Formed by Ultraviolet Photoreduction of Silica-Supported Chromium(VI) in Carbon Monoxide," J. Phys. Chem. 1994, 98, pp. 4336-4342.

McDaniel, et. al., "The Activation of the Phillips Polymerization Catalyst; I. Influence of the Hydroxyl Population", J. Catalysis, vol. 82, No. 1, Jul. 1, 1983, pp. 98-109.

Milas, N .A., The hydroxylation of unsaturated substances. III. The use of vanadium pentoxide and chromium trioxide as Catalysts of hydroxylation, The Journal of the American Chemical Society, vol. 59, No. 11, pp. 2342-2344 (Year: 1937).

Milas, N.A. et al., The hydroxylation of unsaturated substances. IV. The catalytic hydroxylation of unsaturated hydrocarbons, The Journal of the American Chemical Society, vol. 59, No. 11, pp. 2345-2347 (Year: 1937).

Mino, et al., "Photoinduced Ethylene Polymerization on the CrVI/SiO2 Phillips Catalyst," J. Phys. Chem. C 2019, 123, 13 pp. 8145-8152.

Monwar, et.al., "Ethylene polymerization by hydrocarbon-reduced Cr/silica catalyst", Journal of Catalysis 394 (2021) 451-464.

Myers, et al. "Silica-Supported Chromium Catalysts for Ethylene Polymerization: The Active Oxidation States of Chromium." Journal of Catalysts, vol. 99, No. 1. May 1, 1986.

Potter, et al., "Reduction of the Phillips Catalyst by Various Olefins: Stoichiometry, Thermochemistry, Reaction Products and Polymerization Activity", J. Catal. 344 (2016) 657-668.

(56) References Cited

OTHER PUBLICATIONS

Schwerdtfeger, E., et al., Reduction of Cr(VI) polymerization catalysts by non-olefinic hydrocarbons, Applied Catalysis A: General, 423-424, pp. 91-99 (Year: 2012).
Scott, et al. "Surface Organometallic Investigation of the Mechanism of Ethylene Polymerization by Silica-Supported Cr Catalysts", J. Chem. Eng. Sci. 2001, 56, 4155-4163.
Thompson, et al. "'Sigma-Bond metathesis' for carbon-hydrogen bonds of hydrocarbons and Sc—R (R=H, alkyl, aryl) bonds of permethylscandocene derivatives. Evidence for noninvolvement of the pi system in electrophilic activation of aromatic and vinylic C—H bonds", J. Am. Chem. Soc. 1987, 109, 203-219.
Vidal, et al. "Metathesis of Alkanes Catalyzed by Silica-Supported Transition Metal Hydrides." Science, American Association for the Advancement of Science, US, vol. 276, No. 5309. Apr. 4, 1997. pp. 99-102.
Weckhuysen et al., "Alkane dehydrogenation over supported chromium oxide catalysts," Catalysis Today 51 (1999) pp. 223-232.
Welch, et. al., "The Activation of the Phillips Polymerization Catalyst; II. Activation by Reduction-Reoxidation", J Catalysis, vol. 82, No. 1, Jul. 1, 1983, pp. 110-117.
Wikipedia, Ultraviolet, Oct. 2019, p. 1-17 (Year: 2019).
Wikipedia. "Chromium(I) Hydride." https://en.wikipedia.org/w/index.php?title=Chromium(I)_hyride&oldid=837482511.
Zhu, et al., "Synthesis and Structural Characterization of M(PMe3)3(O2CR)2(OH2)H2 (M) Mo, W): Aqua-Hydride Complexes of Molybdenum and Tungsten", Inorg. Chem. 2005, 44, 9637-9639.

\* cited by examiner

CHROMIUM-BASED CATALYSTS AND PROCESSES FOR CONVERTING ALKANES INTO HIGHER AND LOWER ALIPHATIC HYDROCARBONS

REFERENCE TO RELATED APPLICATION

This application is a continuation application of U.S. patent application Ser. No. 17/013,912, filed on Sep. 8, 2020, now U.S. Pat. No. 11,396,485, which claims the benefit of U.S. Provisional Patent Application No. 62/900,683, filed on Sep. 16, 2019, the disclosures of which are incorporated herein by reference in their entirety.

FIELD OF THE INVENTION

The present disclosure generally relates to methods for cracking an alkane reactant to form a lower aliphatic hydrocarbon product, and to methods for converting an alkane reactant into a higher aliphatic hydrocarbon product. More particularly, the present disclosure relates to performing such methods with a supported chromium (II) catalyst.

BACKGROUND OF THE INVENTION

Alkylation Units (AUs) are generally used to upgrade the octane value of low molecular weight hydrocarbons and alkenes into higher value gasoline components, such as isoheptane and isooctane. These AUs rely on the use of sulfuric (SAAU) or hydrofluoric (HFAU) acids to affect this conversion. AUs generally operate at temperatures of less than 30° C.

Fluid catalytic cracking units (FCCUs) are used to convert components of crude oil with boiling points over 300° C. into much shorter hydrocarbon molecules. FCCUs operate at temperatures of around 550° C. and use catalysts consisting of zeolites or aluminas as well as a support matrix (binder). Transition metals are generally detrimental to the catalyst activity and performance.

It would be beneficial to convert alkanes into both higher and lower molecular weight hydrocarbons without the use of either strong acids or very high operating temperatures. Accordingly, it is to this ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

In one aspect of this invention, a process for cracking an alkane reactant to form a lower aliphatic hydrocarbon product is disclosed, and in this aspect, the process can comprise contacting the alkane reactant with a supported chromium (II) catalyst to form the lower aliphatic hydrocarbon product, wherein the lower aliphatic hydrocarbon product has a molecular weight less than that of the alkane reactant. In another aspect of this invention, a process for converting an alkane reactant into a higher aliphatic hydrocarbon product is disclosed, and in this aspect, the process can comprise contacting the alkane reactant with a supported chromium (II) catalyst to form the higher aliphatic hydrocarbon product, wherein the higher aliphatic hydrocarbon product has a molecular weight greater than that of the alkane reactant. In further aspects, these processes can produce, concurrently, both a lower aliphatic hydrocarbon product and a higher aliphatic hydrocarbon product.

The resultant aliphatic hydrocarbon products can contain, unexpectedly, a mixture of various aliphatic hydrocarbons (such as linear alkanes, branched alkanes, 1-alkenes, and internal alkenes), aromatic hydrocarbons, and hydrogen.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the catalysts, compositions, processes, or methods described herein are contemplated with or without explicit description of the particular combination. Additionally, unless explicitly recited otherwise, any aspect or feature disclosed herein can be combined to describe inventive catalysts, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

In this disclosure, while catalysts, compositions, processes, and methods are described in terms of "comprising" various components or steps, the catalysts, compositions, processes, and methods also can "consist essentially of" or "consist of" the various components or steps, unless stated otherwise.

The terms "a," "an," and "the" are intended to include plural alternatives, e.g., at least one. For instance, the disclosure of "an alkane," "a catalyst," etc., is meant to encompass one, or mixtures or combinations of more than one, alkane, catalyst, etc., unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical compound having a certain number of carbon atoms is disclosed or claimed, the intent is to disclose or claim individually every possible number that such a range could encompass, consistent with the disclosure herein. For example, the disclosure that a product contains a $C_1$ to $C_{18}$ aliphatic hydrocarbon compound, or in alternative language, an aliphatic hydrocarbon compound having from 1 to 18 carbon atoms, as used herein, refers to a compound that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ aliphatic hydrocarbon compound), and also including any combination of ranges between these two numbers (for example, a $C_2$ to $C_4$ aliphatic hydrocarbon compound and a $C_{12}$ to $C_{16}$ aliphatic hydrocarbon compound).

Similarly, another representative example follows for the amount of chromium on the supported catalyst consistent with aspects of this invention. By a disclosure that the amount of chromium can be in a range from about 0.1 to about 15 wt. %, the intent is to recite that the amount of chromium can be any amount in the range and, for example, can be equal to about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, or about 15 wt. %. Additionally, the amount of chromium can be within any range from about 0.1 to about 15 wt. % (for example, from about 0.1 to about 5 wt. %), and this also includes any combination of ranges between about 0.1 and about 15 wt. % (for example, the amount of chromium can be in a range from about 0.5 to about 2.5 wt. %, or from about 5 to about 15 wt. %). Further, in all instances, where "about" a particular value is disclosed, then that value itself is disclosed. Thus, the disclosure that the amount of chromium can be from about 0.1 to about 15 wt. % also discloses an amount of chromium from 0.1 to 15 wt. % (for example, from 0.1 to 5 wt. %), and this also includes any combination of ranges between 0.1 and 15 wt. % (for example, the amount of chromium can be in a range from 0.5 to 2.5 wt. %, or from 5 to 15 wt. %). Likewise, all other ranges disclosed herein should be interpreted in a manner similar to these examples.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, and often within 5% of the reported numerical value.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is generally directed to the use of supported chromium (II) catalysts to convert an alkane into a lower molecular weight aliphatic hydrocarbon (cracking), a higher molecular weight aliphatic hydrocarbon, or both. Unexpectedly, it was found that the processes and catalysts disclosed herein can efficiently convert the alkane into other aliphatic hydrocarbons at temperatures of less than 300° C., and beneficially, even at ambient temperature. Also surprisingly, aromatic hydrocarbons and hydrogen gas can be formed, in addition to the lower and higher molecular weight aliphatic hydrocarbons.

Processes for Forming ALiphatic Hydrocarbon Products

Aspects of this invention are directed to processes for converting an alkane reactant into a lower aliphatic hydrocarbon product, into a higher aliphatic hydrocarbon product, or into both a lower aliphatic hydrocarbon product and a higher aliphatic hydrocarbon product. A first process for cracking an alkane reactant to form a lower aliphatic hydrocarbon product consistent with aspects of this invention can comprise contacting the alkane reactant with a supported chromium (II) catalyst to form the lower aliphatic hydrocarbon product, wherein the lower aliphatic hydrocarbon product has a molecular weight less than that of the alkane reactant. In this disclosure, the lower aliphatic hydrocarbon product can be referred to as a first aliphatic hydrocarbon product; thus, the first aliphatic hydrocarbon product has a molecular weight less than that of the alkane reactant.

A second process for converting an alkane reactant into a higher aliphatic hydrocarbon product consistent with aspects of this invention can comprise contacting the alkane reactant with a supported chromium (II) catalyst to form the higher aliphatic hydrocarbon product, wherein the higher aliphatic hydrocarbon product has a molecular weight greater than that of the alkane reactant. In this disclosure, the higher aliphatic hydrocarbon product can be referred to as a second aliphatic hydrocarbon product; thus, the second aliphatic hydrocarbon product has a molecular weight greater than that of the alkane reactant.

A third process for converting an alkane reactant into a lower aliphatic hydrocarbon product and a higher aliphatic hydrocarbon product consistent with aspects of this invention can comprise contacting the alkane reactant with a supported chromium (II) catalyst to form (both) the lower aliphatic hydrocarbon product and the higher aliphatic hydrocarbon product. As above, the lower (or first) aliphatic hydrocarbon product has a molecular weight less than that of the alkane reactant, while the higher (or second) aliphatic hydrocarbon product has a molecular weight greater than that of the alkane reactant.

Generally, the features of the first process, the second process, and the third process (e.g., the alkane reactant, the supported chromium (II) catalyst, the lower aliphatic hydrocarbon product, the higher aliphatic hydrocarbon product, and the conditions under which the lower and/or higher aliphatic hydrocarbon product is formed, among others) are independently described herein and these features can be combined in any combination to further describe the disclosed processes to produce aliphatic hydrocarbon products. Moreover, additional process steps can be performed before, during, and/or after any of the steps in any of the processes disclosed herein, and can be utilized without limitation and in any combination to further describe these processes, unless stated otherwise. Further, any lower aliphatic hydrocarbon products and/or higher aliphatic hydrocarbon products produced in accordance with the disclosed processes are within the scope of this disclosure and are encompassed herein.

Referring now to the first process, the alkane reactant can be contacted with a supported chromium (II) catalyst to form the lower aliphatic hydrocarbon product, and the lower aliphatic hydrocarbon product has a molecular weight less than that of the alkane reactant. The lower aliphatic hydrocarbon product can include a single aliphatic hydrocarbon compound having a lower molecular weight (e.g., lower carbon number) than that of the alkane reactant, as well as a mixture of aliphatic hydrocarbon compounds having a lower molecular weight than that of the alkane reactant. For example, when the alkane reactant comprises a $C_n$ alkane compound, then the lower aliphatic hydrocarbon product comprises a $(C_{n-1})-$ aliphatic hydrocarbon compound. As a particular example, when $C_n$ is a $C_5$ (n is equal to 5, such as for isopentane), then the term "$(C_{n-1})-$ aliphatic hydrocarbon compound" encompasses any $C_4$ and below ($C_3$, $C_2$, and $C_1$) aliphatic hydrocarbon compound and mixtures of $C_4$ and below ($C_3$, $C_2$, and $C_1$) aliphatic hydrocarbon compounds.

A variety of aliphatic hydrocarbon products can be produced in the first process, inclusive of saturated aliphatic hydrocarbon compounds, unsaturated aliphatic hydrocarbon compounds, linear aliphatic hydrocarbon compounds, branched aliphatic hydrocarbon compounds, and cyclic aliphatic hydrocarbon compounds, as well as combinations thereof. In one aspect, for instance, the alkane reactant can comprise a $C_n$ alkane compound, and the lower aliphatic hydrocarbon product can comprises a mixture of $(C_{n-1})-$ saturated or unsaturated, linear, branched, or cyclic, aliphatic hydrocarbon compounds. In another aspect, the alkane reactant can comprise a $C_n$ alkane compound, and the lower aliphatic hydrocarbon product can comprise a $(C_{-1})-$ internal alkene, a $(C_{n-1})-$ 1-alkene, or a combination of two or more alkenes (further, each alkene, independently, can be linear or branched). In yet another aspect, the alkane reactant can comprise a $C_n$ alkane compound, and the lower aliphatic hydrocarbon product can comprise a $(C_{n-1})-$ linear alkane, a $(C_{n-1})-$ branched alkane, a $(C_{n-1})-$ cyclic alkane, or a combination of two or more alkanes.

In addition to the formation of the lower aliphatic hydrocarbon product, the first process also can further produce $H_2$, can further produce an isomer of the alkane reactant (same carbon number), or can further produce an aromatic compound (e.g., benzene, toluene, xylene(s), ethylbenzene, and the like), as well as any combination of $H_2$, isomer(s) of the alkane reactant, and/or aromatic compound(s).

Thus, the lower aliphatic hydrocarbon product can contain, either singly or in any combination: a lower carbon number linear alkane, a lower carbon number branched alkane, a lower carbon number cyclic alkane, a lower carbon number internal alkene, a lower carbon number 1-alkene, a lower carbon number cyclic alkene, a lower carbon number aromatic compound, an isomer of the alkane reactant at the same carbon number, and/or $H_2$. The term "lower" refers to less than that of alkane reactant.

Referring now to the second process, the alkane reactant can be contacted with a supported chromium (II) catalyst to form the higher aliphatic hydrocarbon product, and the higher aliphatic hydrocarbon product has a molecular weight greater than that of the alkane reactant. The higher aliphatic hydrocarbon product can include a single aliphatic hydrocarbon compound having a higher molecular weight (e.g., higher carbon number) than that of the alkane reactant, as well as a mixture of aliphatic hydrocarbon compounds having a higher molecular weight than that of the alkane reactant. For example, when the alkane reactant comprises a $C_n$ alkane compound, then the higher aliphatic hydrocarbon product comprises a $(C_{n+1})+$ aliphatic hydrocarbon compound. As a particular example, when $C_n$ is a $C_5$ (n is equal to 5, such as for isopentane), then the term "$(C_{n+1})+$ aliphatic hydrocarbon compound" encompasses any $C_6$ and above ($C_7$, $C_8$, $C_9$, $C_{10}$, and so forth) aliphatic hydrocarbon compound and mixtures of $C_6$ and above ($C_7$, $C_8$, $C_9$, $C_{10}$, and so forth) aliphatic hydrocarbon compounds.

A variety of aliphatic hydrocarbon products can be produced in the second process, inclusive of saturated aliphatic hydrocarbon compounds, unsaturated aliphatic hydrocarbon compounds, linear aliphatic hydrocarbon compounds, branched aliphatic hydrocarbon compounds, and cyclic aliphatic hydrocarbon compounds, as well as combinations thereof. In one aspect, for instance, the alkane reactant can comprise a $C_n$ alkane compound, and the higher aliphatic hydrocarbon product can comprises a mixture of $(C_{n+1})+$ saturated or unsaturated, linear, branched, or cyclic, aliphatic hydrocarbon compounds. In another aspect, the alkane reactant can comprise a $C_n$ alkane compound, and the higher aliphatic hydrocarbon product can comprise a $(C_{n+1})+$ internal alkene, a $(C_{n+1})+$ 1-alkene, or a combination of two or more alkenes (further, each alkene, independently, can be linear or branched). In yet another aspect, the alkane reactant can comprise a $C_n$ alkane compound, and the higher aliphatic hydrocarbon product can comprise a $(C_{n+1})+$ linear alkane, a $(C_{n+1})+$ branched alkane, a $(C_{n+1})+$ cyclic alkane, or a combination of two or more alkanes.

In addition to the formation of the higher aliphatic hydrocarbon product, the second process also can further produce $H_2$, can further produce an isomer of the alkane reactant (same carbon number), or can further produce an aromatic compound (e.g., benzene, toluene, xylene(s), ethylbenzene, and the like), as well as any combination of $H_2$, isomer(s) of the alkane reactant, and/or aromatic compound(s).

Thus, the higher aliphatic hydrocarbon product can contain, either singly or in any combination: a higher carbon number linear alkane, a higher carbon number branched alkane, a higher carbon number cyclic alkane, a higher carbon number internal alkene, a higher carbon number 1-alkene, a higher carbon number cyclic alkene, a higher carbon number aromatic compound, an isomer of the alkane reactant at the same carbon number, and/or $H_2$. The term "higher" refers to greater than that of alkane reactant.

For the first process, the second process, and the third process, the alkane reactant can comprise a $C_n$ alkane compound, the lower aliphatic hydrocarbon product can comprise a $(C_{n-1})-$ aliphatic hydrocarbon compound, and the higher aliphatic hydrocarbon product can comprise a $(C_{n+1})+$ aliphatic hydrocarbon compound. While not being limited thereto, the integer n often can range from 1 to 36, such as from 1 to 12, from 1 to 8, from 1 to 6, from 2 to 18, from 2 to 12, from 2 to 8, or from 2 to 6.

Therefore, the alkane reactant can comprise any suitable carbon number alkane compound, for instance, a $C_1$ to $C_{36}$ alkane compound; alternatively, a $C_1$ to $C_{12}$ alkane compound; alternatively, a $C_1$ to $C_6$ alkane compound; alternatively, a $C_2$ to $C_{18}$ alkane compound; alternatively, a $C_2$ to $C_{12}$ alkane compound; or alternatively, a $C_2$ to $C_8$ alkane compound. If desired, the alkane reactant can contain a single alkane compound (for example, ethane) of relatively high purity, such as at least about 95 wt. % of a single alkane compound, at least about 98 wt. % of a single alkane compound, at least about 99 wt. % of a single alkane compound, or at least about 99.5 wt. % of a single alkane compound, and so forth.

Alternatively, the alkane reactant used in the first process, the second process, or the third process, can comprise any suitable mixture of two or more alkane compounds, for instance, a mixture of $C_1$ to $C_{18}$ alkane compounds, a mixture of $C_1$ to $C_4$ alkane compounds, a mixture of $C_2$ to $C_6$ alkane compounds, a mixture of $C_6$ to $C_8$ alkane compounds, or a mixture of $C_{10}$ to $C_{14}$ alkane compounds, and the like. In circumstances where a mixture of alkane compounds is used as the alkane reactant, a weight-average (Mw) molecular weight of the alkane reactant can be determined. For the first process, in which a lower aliphatic hydrocarbon product is formed, the lower aliphatic hydrocarbon product would therefore have a weight-average molecular weight less than the Mw of the alkane reactant. Conversely, for the second process, in which a higher aliphatic hydrocarbon product is formed, the higher aliphatic hydrocarbon product would therefore have a weight-average molecular weight greater than the Mw of the alkane reactant.

In addition to the carbon number, the alkane reactant can be categorized as a cyclic alkane, a linear alkane, or a branched alkane. Hence, the alkane reactant in one aspect can be a cyclic alkane, a linear alkane in another aspect, and a branched alkane in yet another aspect.

Illustrative examples of alkane reactants can include methane, ethane, propane, butane (e.g., n-butane or isobutane), pentane (e.g., n-pentane, neopentane, or isopentane), hexane, heptane, octane, nonane, decane, undecane, dodecane, tridecane, tetradecane, pentadecane, hexadecane, heptadecane, octadecane, and the like, as we well as combinations thereof. In a non-limiting aspect, the alkane reactant can comprise methane; alternatively, ethane; alternatively, propane; alternatively, butane; alternatively, pentane; alternatively, hexane; alternatively, heptane; alternatively, octane; alternatively, nonane; alternatively, decane; alternatively, undecane; alternatively, dodecane; alternatively, tridecane; alternatively, tetradecane; alternatively, pentadecane; alternatively, hexadecane; alternatively, heptadecane; or alternatively, octadecane. In another aspect, the alkane reactant can comprise ethane, propane, n-butane, isobutane, n-pentane, neopentane, isopentane, n-hexane, n-heptane, n-octane, n-decane, n-dodecane, and the like, or any combination thereof, while in another aspect, the alkane reactant can comprise propane, n-butane, isobutane, n-pentane, neopentane, isopentane, n-hexane, n-heptane, n-octane, n-decane, n-dodecane, and the like, or any combination thereof. In yet another aspect, the alkane reactant can comprise methane, ethane, propane, butane (e.g., n-butane or isobutane), pentane (e.g., n-pentane, neopentane, or isopentane), or any combination thereof or alternatively, the alkane reactant can comprise methane, ethane, propane, butane (e.g., n-butane or isobutane), or any combination thereof.

The processes to produce the lower aliphatic hydrocarbon product and/or the higher aliphatic hydrocarbon product can be conducted at any suitable temperature and for any suitable period of time. Representative and non-limiting ranges for the temperature of contacting the supported chromium catalyst and the alkane reactant and/or for forming the lower aliphatic hydrocarbon product and/or the higher aliphatic hydrocarbon product can include from about 0° C. to about 800° C., from about 0° C. to about 350° C., from about 10° C. to about 350° C., from about 20° C. to about 350° C., from about 10° C. to about 300° C., from about 20° C. to about 300° C., from about 10° C. to about 250° C., from about 20° C. to about 250° C., from about 10° C. to about 200° C., from about 100° C. to about 600° C., from about 100° C. to about 200° C., or from about 300° C. to about 600° C. These temperature ranges also are meant to encompass circumstances where the first process, the second process, and the third process are performed at a series of different temperatures, instead of at a single fixed temperature, falling within the respective temperature ranges, wherein at least one temperature is within the recited ranges.

Similarly, the time period for contacting the supported catalyst and the alkane reactant, or for the formation of the lower and/or higher aliphatic hydrocarbon product, is not particularly limited, and can be conducted for any suitable period of time. In some aspects, the time period can be least about 1 sec, at least about 2 sec, at least about 5 sec, at least about 10 sec, at least about 30 sec, or at least about 1 min. In other aspects, the time period can be from about 1 sec to about 48 hr, from about 2 sec to about 24 hr, from about 5 sec to about 8 hr, from about 10 sec to about 8 hr, or from about 5 sec to about 1 hr.

Often, the process for forming the aliphatic hydrocarbon products can be a flow process and/or a continuous process.

In such circumstances, the alkane reactant-catalyst contact time (or reaction time) can be expressed in terms of weight hourly space velocity (WHSV)—the ratio of the weight of the alkane reactant which comes in contact with a given weight of catalyst per unit time (units of g/g/hr, or $hr^{-1}$).

While not limited thereto, the WHSV employed for the first process, the second process, and the third process can have a minimum value of 0.01 $hr^{-1}$, 0.02 $hr^{-1}$, 0.05 $hu^{-1}$, 0.1 $hr^{-1}$, 0.25 $hr^{-1}$, or 0.5 $hr^{-1}$; or alternatively, a maximum value of 500 $hr^{-1}$, 400 $hr^{-1}$, 300 $hr^{-1}$, 100 $hr^{-1}$, 50 $hr^{-1}$, 10 $hr^{-1}$, 5 $hr^{-1}$, 2 $hr^{-1}$, or 1 $hr^{-1}$. Generally, the WHSV can be in a range from any minimum WHSV disclosed herein to any maximum WHSV disclosed herein. In a non-limiting aspect, the WHSV can be in a range from about 0.01 $hr^{-1}$ to about 500 $hr^-$; alternatively, from about 0.01 $hu^{-1}$ to about 10 $hr^{-1}$; alternatively, from about 0.01 $hr^{-1}$ to about 1 $hr^-$; alternatively, from about 0.02 $hr^{-1}$ to about 400 $hr^{-1}$; alternatively, from about 0.02 $hr^{-1}$ to about 50 $hr^{-1}$; alternatively, from about 0.05 $hr^{-1}$ to about 300 $hr^{-1}$; alternatively, from about 0.05 $hr^{-1}$ to about 5 $hr^{-1}$; alternatively, from about 0.1 $hr^{-1}$ to about 400 $hr^{-1}$; alternatively, from about 0.25 $hr^-$ to about 50 $hu^{-1}$; alternatively, from about 0.25 $hr^{-1}$ to about 2 $hr^{-1}$; alternatively, from about 0.5 $hr^{-1}$ to about 400 $hr^{-1}$; alternatively, from about 0.5 $hr^{-1}$ to about 5 $hr^{-1}$; or alternatively, from about 0.5 $hr^{-1}$ to about 2 $hr^{-1}$. Other WHSV ranges are readily apparent from this disclosure.

Any suitable reactor or vessel can be used to form the lower and/or higher aliphatic hydrocarbon product, non-limiting examples of which can include a flow reactor, a continuous reactor, a packed bed reactor, a fluidized bed reactor, and a stirred tank reactor, including more than one reactor in series or in parallel, and including any combination of reactor types and arrangements.

In one aspect, the disclosed processes can comprise contacting the alkane reactant in the gas phase with the solid supported catalyst. In another aspect, the disclosed processes can comprise contacting the alkane reactant in the liquid phase with the solid supported catalyst. In another aspect, the disclosed processes can comprise a slurry (e.g., a loop slurry) of the solid supported catalyst in the alkane reactant. In yet another aspect, the disclosed processes can comprise contacting the alkane reactant with a fluidized bed of the solid supported catalyst. In still another aspect, the disclosed processes can comprise contacting the alkane reactant (e.g., in the gas phase or in the liquid phase) with a fixed bed of the solid supported catalyst. Any suitable pressure can be used to contact the alkane reactant and the supported catalyst and to form the aliphatic hydrocarbon products, and such can depend upon the carbon number of the alkane reactant (and its boiling point), the type of reactor configuration and desired mode for contacting the reactant with the solid catalyst, amongst other considerations.

The weight ratio of the alkane reactant to chromium (of the supported chromium catalyst) is not particularly limited, and generally can fall within a range from about 5:1 to about 1000:1. Typical ranges for the weight ratio can include, but are not limited to, from about 5:1 to about 500:1, from about 10:1 to about 1000:1, from about 10:1 to about 500:1, from about 15:1 to about 750:1, or from about 15:1 to about 150:1.

The processes described herein result in an unexpectedly high conversion of the alkane reactant and/or yield to the lower aliphatic hydrocarbon product and/or yield to the higher aliphatic hydrocarbon product. In one aspect, the minimum conversion (or yield) can be at least about 2 wt. %, at least about 5 wt. %, at least about 10 wt. %, at least about 15 wt. %, or at least about 25 wt. %. Additionally, the maximum conversion (or yield) can be about 50 wt. %, about 70 wt. %, about 80 wt. %, about 90 wt. %, about 95 wt. %, or about 99 wt. %, and can approach 100% conversion of the alkane reactant (or yield of the lower aliphatic hydrocarbon product and/or the higher aliphatic hydrocarbon product). Generally, the conversion (or yield) can be in a range from any minimum conversion (or yield) disclosed herein to any maximum conversion (or yield) disclosed herein. Non-limiting ranges of conversion (or yield) can include from about 5 wt. % to about 99 wt. %, from about 10 wt. % to about 95 wt. %, or from about 15 wt. % to about 70 wt. %. For conversion, the percentages are the amount of the alkane reactant converted based on the initial amount of the alkane reactant. The yield values are weight percentages, and are based on the weight of the aliphatic hydrocarbon compound(s) produced to the weight of alkane reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor).

Also unexpectedly, continuous flow processes for producing the lower aliphatic hydrocarbon product and/or the higher aliphatic hydrocarbon product in accordance with this invention have unexpectedly high single pass conversions of the alkane reactant (or single pass yields to the desired lower aliphatic hydrocarbon product and/or the higher aliphatic hydrocarbon product). In one aspect, the minimum single pass conversion (or yield) can be at least about 0.5 wt. %, at least about 1 wt. %, at least about 2 wt. %, at least about 5 wt. %, at least about 10 wt. %, at least about 15 wt. %, or at least about 25 wt. %. Additionally, the maximum single pass conversion (or yield) can be about 50 wt. %, about 70 wt. %, about 80 wt. %, about 90 wt. %, about 95 wt. %, or about 99 wt. %, and can approach 100% conversion of the alkane reactant (or yield of the lower aliphatic hydrocarbon product and/or the higher aliphatic hydrocarbon product), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from about 5 wt. % to about 99 wt. %, from about 10 wt. % to about 95 wt. %, or from about 15 wt. % to about 70 wt. %.

Unlike certain alkylation processes, a mineral acid is not required in the first process, the second process, and the third process. Thus, these processes do not require the use of sulfuric acid, hydrofluoric acid, and the like, in order to produce the lower aliphatic hydrocarbon products and/or the higher aliphatic hydrocarbon products.

The processes to produce the lower aliphatic hydrocarbon products and/or the higher aliphatic hydrocarbon products disclosed herein typically can result in a crude reaction mixture containing a desired product, residual alkane reactant, and other hydrocarbon products, and optionally hydrogen. In many instances, it can be desirable to isolate or separate at least a portion (and in some cases, all) of the alkane reactant from the lower aliphatic hydrocarbon product (or the higher aliphatic hydrocarbon product). This can be accomplished using any suitable technique, which can include but is not limited to, extraction, filtration, evaporation, or distillation, as well as combinations of two or more of these techniques. In particular aspects of this invention, the isolating or separating step utilizes distillation at any suitable pressure (one or more than one distillation column can be used).

Additionally, certain components of the reaction mixture—such as the alkane reactant—can be recovered and recycled to the reactor. In such instances, the alkane reactant can be recycled and contacted with supported chromium catalyst again, such that the overall conversion of the alkane product is increased after multiple contacts with the supported chromium (II) catalyst (or multiple passes through the reactor containing the catalyst).

It is contemplated that after a suitable period of time and usage (e.g., contact with the alkane reactant), the supported chromium (II) catalyst will have to be regenerated. Thus, the first process, the second process, and the third process can further comprise a step of regenerating at least a portion (and in some cases, all) of the supported chromium (II) catalyst. Any suitable regeneration process can be used, and such can include a step of CO reduction.

If desired, the first process, second process, and third process can further comprise a step of forming the supported chromium (II) catalyst prior to contacting the supported chromium (II) catalyst with the alkane reactant. In such aspects, the processes disclosed herein can further comprise a step of reducing a supported chromium (VI) catalyst to form the supported chromium (II) catalyst. Various suitable techniques can be used, such as CO reduction, either by light or by elevated temperature, or a combination thereof.

Chromium Catalysts

The supported chromium (II) catalyst utilized in the first process, the second process, and the third process is not particularly limited, but generally can be an inorganic chromium (II) catalyst, such as a supported chromium (II) oxide catalyst. The amount of chromium in the supported chromium catalyst also is not particularly limited. However, the amount of chromium in the supported chromium catalyst typically ranges from about 0.01 to about 50 wt. %; alternatively, from about 0.01 to about 20 wt. %; alternatively, from about 0.01 to about 10 wt. %; alternatively, from about 0.05 to about 15 wt. %; alternatively, from about 0.1 to about 15 wt. %; alternatively, from about 0.2 to about 10 wt. %; alternatively, from about 0.1 to about 5 wt. %; alternatively, from about 0.5 to about 30 wt. %; or alternatively, from about 0.5 to about 2.5 wt. %. These weight percentages are based on the amount of chromium relative to the total weight of the supported catalyst.

Likewise, the amount of chromium (II) in the supported chromium catalyst is not particularly limited, and can fall within the same ranges. Thus, the supported catalyst can contain from about 0.01 to about 50 wt. %, from about 0.01 to about 20 wt. %, from about 0.01 to about 10 wt. %, from about 0.05 to about 15 wt. %, from about 0.1 to about 15 wt. %, from about 0.2 to about 10 wt. %, from about 0.1 to about 5 wt. %, from about 0.5 to about 30 wt. %, or from about 0.5 to about 2.5 wt. % of chromium (II), based on the total weight of the supported catalyst.

Generally, at least about 20 wt. % of the chromium in the supported chromium catalyst is present in an oxidation state of +2 (II), and more often at least about 50 wt. % is present as chromium (II). In further aspects, at least about 75 wt. %, at least about 85 wt.

%, at least about 90 wt. %, or at least about 95 wt. %, of the chromium in the supported chromium catalyst can be present in an oxidation state of +2. These weight percentages are based on the total amount of chromium. Such chromium (II) catalysts usually have a green, blue-green, or blue color.

Conversely, less than or equal to about 50 wt. % of the chromium in the supported chromium catalyst is typically present in an oxidation state of +6 (VI), and more often less than or equal to about 35 wt. %. In further aspects, less than or equal to about 20 wt. %, less than or equal to about 10 wt. %, or less than or equal to 5 wt. %, of chromium in the supported catalyst can be present in an oxidation state of +6. The minimum amount of chromium (VI) often can be 0 wt. % (no measurable amount), at least about 0.5 wt. %, at least about 1 wt. %, at least about 2 wt. %, or at least about 3 wt. %. These weight percentages are based on the total amount of chromium. Traditional chromium (VI) catalysts often will have an orange, yellow, or tan color.

Additionally or alternatively, the chromium in the supported chromium (II) catalyst can be characterized by an average valence of less than or equal to 3.5. More often, the chromium in the supported chromium (II) catalyst has an average valence of less than or equal to 3.25, or alternatively, an average valence of less than or equal to 3.

The total pore volume of the supported chromium catalyst also is not particularly limited. For instance, the supported chromium catalyst can have a total pore volume in a range from about 0.1 to about 5 mL/g, from about 0.15 to about 5 mL/g, from about 0.1 to about 3 mL/g, from about 0.5 to about 2.5 mL/g, or from about 0.15 to about 2 mL/g. Likewise, the surface area of the supported chromium catalyst is not limited to any particular range. Generally, however, the supported chromium catalyst can have a BET surface area in a range from about 50 to about 2000 $m^2/g$, from about 50 to about 700 $m^2/g$, from about 50 to about 400 $m^2/g$, from about 100 to about 1200 $m^2/g$, from about 150 to about 525 $m^2/g$, or from about 200 to about 400 $m^2/g$. BET surface areas are determined using the BET nitrogen adsorption method of Brunaur et al., *J. Am. Chem. Soc.*, 60, 309 (1938), as described in ASTM D1993-91. Total pore volumes are determined in accordance with Halsey, G. D., *J. Chem. Phys.* (1948), 16, pp. 931.

The supported chromium catalyst can have any suitable shape or form, and such can depend on the type of process that is employed to convert the alkane reactant into the lower and/or higher aliphatic hydrocarbon product (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadralobe, ring, wagon wheel, monolith, and the like, as well as any combination thereof. Accordingly, various methods can be utilized to prepare the supported catalyst particles, including, for example, extrusion, spray drying, pelletizing, marumerizing, spherodizing, agglomeration, oil drop, and the like, as well as combinations thereof.

In some aspects, the supported chromium catalyst has a relatively small particle size, in which representative ranges for the average (d50) particle size of the supported chromium catalyst can include from about 10 to about 500 microns, from about 25 to about 250 microns, from about 20 to about 100 microns, from about 40 to about 160 microns, or from about 40 to about 120 microns. The d50 particle size, or median or average particle size, refers to the particle size for which 50% of the sample has a smaller size and 50% of the sample has a larger size, and is determined using laser diffraction in accordance with ISO 13320.

In other aspects, the supported catalyst can be in the form of pellets or beads—and the like—having an average size ranging from about 1/16 inch to about 1/2 inch, or from about 1/8 inch to about 1/4 inch. As noted above, the size of the supported chromium (II) catalyst particles can be varied to suit the particular process for converting the alkane reactant into the lower and/or higher aliphatic hydrocarbon product.

Various solid supports can be used for the supported chromium catalyst, such as conventional solid oxides and zeolites. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr. Illustrative examples of solid oxide materials or compounds that can be used as solid support can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as silica, "mixed oxide" compounds thereof such as silica-titania, and combinations or mixtures of more than one solid oxide material. Mixed oxides such as silica-titania can be single or multiple chemical phases with more than one metal combined with oxygen to form the solid oxide. Examples of mixed oxides that can be used as solid oxide include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. In some aspects, the solid support can comprise silica, silica-alumina, silica-coated alumina, silica-titania, silica-titania-magnesia, silica-zirconia, silica-magnesia, silica-boria, aluminophosphate-silica, and the like, or any combination thereof. Silica-coated aluminas are encompassed herein; such oxide materials are described in, for example, U.S. Pat. Nos. 7,884,163 and 9,023,959, incorporated herein by reference in their entirety.

The percentage of each oxide in a mixed oxide can vary depending upon the respective oxide materials. As an example, a silica-alumina (or silica-coated alumina) typically has an alumina content from 5 wt. % to 95 wt. %. According to one aspect, the alumina content of the silica-alumina (or silica-coated alumina) can be from 5 wt. % alumina 50 wt. % alumina, or from 8 wt. % to 30 wt. % alumina. In another aspect, high alumina content silica-aluminas (or silica-coated aluminas) can be employed, in which the alumina content of these materials typically ranges from 60 wt. % alumina to 90 wt. % alumina, or from 65 wt. % alumina to 80 wt. % alumina.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, zirconia, magnesia, boria, zinc oxide, a mixed oxide thereof, or any mixture thereof. In yet another aspect, the solid support can comprise silica, alumina, titania, or a combination thereof alternatively, silica; alternatively, alumina; alternatively, titania; alternatively, zirconia; alternatively, magnesia; alternatively, boria; or alternatively, zinc oxide. In still another aspect, the solid oxide can comprise silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, silica-boria, aluminophosphate-silica, titania-zirconia, and the like, or any combination thereof.

Consistent with certain aspects of this invention, the supported chromium (II) catalyst can comprise a chemically-treated solid oxide as the support, and where the chemically-treated solid oxide comprises a solid oxide (any solid oxide disclosed herein) treated with an electron-withdrawing anion (any electron withdrawing anion disclosed herein). The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed.

It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The chemically-treated solid oxide generally can contain from about 1 wt. % to about 30 wt. % of the electron-withdrawing anion, based on the weight of the chemically-treated solid oxide. In particular aspects provided herein, the chemically-treated solid oxide can contain from about 1 to about 20 wt. %, from about 2 wt. % to about 20 wt. %, from about 3 wt. % to about 20 wt. %, from about 2 wt. % to about 15 wt. %, from about 3 wt. % to about 15 wt. %, from about 3 wt. % to about 12 wt. %, or from about 4 wt. % to about 10 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof.

In another aspect, the chemically-treated solid oxide employed in the supported chromium (II) catalysts and processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. Additional information on chemically-treated solid oxide can be found in, for instance, U.S. Pat. Nos. 7,294,599, 7,601,665, 7,884,163, 8,309,485, 8,623,973, and 8,703,886, which are incorporated herein by reference in their entirety.

Representative examples of supported chromium catalysts (in which a solid oxide is the support) include, but are not limited to, chromium (II)/silica, chromium (II)/silica-titania, chromium (II)/silica-titania-magnesia, chromium (II)/silica-alumina, chromium (II)/silica-coated alumina, chromium (II)/aluminophosphate, chromium (II)/alumina, chromium (II)/alumina borate, and the like, or any combination thereof. In one aspect, for instance, the supported chromium catalyst can comprise chromium (II)/silica, while in another aspect, the supported chromium catalyst can comprise chromium (II)/silica-titania, and in yet another aspect, the supported chromium catalyst can comprise chromium (II)/silica-alumina and/or chromium (II)/silica-coated alumina. In circumstances in which the supported chromium catalyst comprises chromium (II)/silica-titania, any suitable amount of titanium can be present, including from about 0.1 to about 20 wt. %, from about 0.5 to about 15 wt. %, from about 1 to about 10 wt. %, or from about 1 to about 6 wt. % titanium, based on the total weight of the supported chromium (II) catalyst.

Representative examples of supported chromium catalysts (in which a chemically-treated solid oxide is the support) include, but are not limited to, chromium (II)/sulfated alumina, chromium (II)/fluorided alumina, chromium (II)/fluorided silica-alumina, chromium (II)/fluorided silica-coated alumina, and the like, as well as combinations thereof.

Consistent with certain aspects of this invention, the supported chromium (II) catalyst can comprise a zeolite as the support, i.e., a chromium (II) supported zeolite. Any suitable zeolite can be used, for instance, large pore and medium pore zeolites. Large pore zeolites often have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often have average pore diameters in a range of from about 5 Å to about 7 Å. Combinations of zeolitic supports can be used.

Additional representative examples of zeolites that can be used in the supported catalyst include, for instance, a ZSM-5 zeolite, a ZSM-11 zeolite, a EU-1 zeolite, a ZSM-23 zeolite, a ZSM-57 zeolite, an ALPO4-11 zeolite, an ALPO4-41 zeolite, and a Ferrierite framework type zeolite, and the like, or any combination thereof.

In the supported chromium (II) catalyst, the zeolite can be bound with a support matrix (or binder), non-limiting examples of which can include silica, alumina, magnesia, boria, titania, zirconia, various clays, and the like, including mixed oxides thereof, as well as mixtures thereof. For example, the supported chromium (II) catalyst support can comprise a binder comprising alumina, silica, a mixed oxide thereof, or a mixture thereof. The zeolite can be bound with the binder using any method known in the art. While not being limited thereto, the catalyst can comprise a zeolite and from about 3 wt. % to about 35 wt. % binder; alternatively, from about 5 wt. % to about 30 wt. % binder; or alternatively, from about 10 wt. % to about 30 wt. % binder. These weight percentages are based on the total weight of the catalyst.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

The alkane reactions of Examples 1-17 and 20-22 were performed as follows. Approximately 20-30 g of the catalyst (Catalyst A to Catalyst M, discussed below) were added to a 2-inch diameter quartz tube containing a coarse sintered glass frit (gas distribution plate) at the bottom. A nitrogen stream was added at the bottom of the tube so that it passed up through the frit and fluidized the catalyst. The flow rate was 0.03-0.1 ft/sec. The tube was placed in a furnace and the temperature controlled at a desired set point for elevated temperature experiments (100-350° C.). For each liquid example, a small sample (20-30 mL) of the alkane reactant was injected on to another sintered glass frit, through which the nitrogen stream passed, thus evaporating the alkane into the nitrogen stream, and contacting it with the fluidized catalyst bed. The residence time in the bed was 5-10 sec.

To start the reaction, the catalyst bed was heated up to the desired temperature. Then, the injection of alkane liquid was made under the bed in a section of the tubing that was at room temperature. It usually took about 30 min for all of it to evaporate and be carried up through the catalyst bed. Coming out of the catalyst bed, the gas went through a disengagement zone, where entrained catalyst fell back into the bed. Then it went through a cold trap, usually set at −78° C. Thus, all reaction products exited the top of the tube, including residual alkane reactant, and were passed through a dry ice trap to condense liquid products (condensate). Reaction products and alkane reactant that were not condensed passed though the ice trap into a gas sampling bag (vapor). Samples of the condensate and the vapor were analyzed by GC-MS.

The alkane reactions of Examples 18-19 were performed as follows. Approximately 2 g of catalyst were charged into an air-tight Fisher-Porter bottle under nitrogen. Then, 10-20 mL of liquid pentane was injected into the bottle, followed by mixing at ambient temperature for a contact time of 30 min. Then, the liquid product, referred to as condensate in Table I, was analyzed by GC-MS. For these experiments, the weight hourly space velocity (WHSV)—the ratio of the weight of the alkane reactant which comes in contact with a given weight of catalyst per unit time (units of g/g/hr)—ranged from 1 $hr^{-1}$ to 3 $hr^{-1}$.

The GC-MS procedure for analyzing the vapor product utilized an Agilent model 7890B gas chromatograph which was run at room temperature using six molecular sieve columns. The valving and sequencing protocol was produced by Agilent as a standard RGA package (Refinery Gas Analysis). It detects hydrocarbons of 6 carbons or less, as well as CO, $CO_2$, and $H_2$.

The GC-MS procedure for analyzing the condensate (liquid) product was as follows. Gas chromatography was performed using an Agilent 7890B GC equipped with an all-purpose capillary column (Agilent J&W VF-5 ms, 30 m×0.25 mm×0.25 µm). Approximate 0.5 µL sample aliquots were injected into a GC port held at 250° C. using a split ratio of 10:1. The carrier gas was ultra-high purity helium and was electronically controlled throughout the run to a constant flow rate of 1.2 mL/min. Initial column temperature was held at 50° C. for 5 min, ramped at 20° C./min to 250° C., and then held at 250° C. for 19 min. Spectral assignment was made via mass correlation using an Agilent 5977B mass spectrometer connected to the GC unit using electron ionization at 70 eV. The nominal mass range scanned was 14-400 m/z using a scan time of 0.5 sec. Nominal detector voltage used was 1200 V.

Catalyst A was a Cr/silica-titania cogel catalyst containing 1 wt. % Cr and 2.5% wt. % Ti, with an average particle size of 130 um, a BET surface area of 500 m$^2$/g, and a pore volume of 2.5 mL/g. After calcining in air at 871° C. for 3 hr, the catalyst was subjected to CO reduction at 350° C. for 30 min, then a N$_2$ flush for 30 min at 350° C., to form the chromium (II)/silica-titania catalyst.

Catalyst B was a silica having an average particles size of 100 um, a BET surface area of 500 m$^2$/g, and a pore volume of 1.6 mL/g. Catalyst B was calcined in air at 650° C. for 3 hr prior to use.

Catalyst C was 6 wt. % Cr supported on the silica of Catalyst B. After calcining in air at 450° C. for 3 hr, the catalyst was subjected to a CO reduction at 350° C. for 30 min to form the chromium (II)/silica catalyst.

Catalyst D was the silica-titania support of Catalyst A, but without chromium. After calcining in air at 800° C. for 1 hr, the catalyst was subjected to CO reduction at 420° C. for 30 min.

Catalyst E was the silica of Catalyst B dried at 200° C. overnight. After cooling, the catalyst was slurried in n-heptane, followed by addition of 3.5 wt.% Ti as titanium isopropoxide, and the evaporation of heptane. The catalyst was then calcined in air at 750° C. for 3 hr, then subjected to CO reduction at 500° C. for 1 hr.

Catalyst F was an alumina having an average particle size of 100 um, a BET surface area of 300 m2/g, and a pore volume of 1.1 mL/g. After calcining at 600° C. overnight, impregnation with 15% H$_2$SO$_4$ in water, and spray drying, the catalyst was calcined in air at 600° C. for 3 hr.

Catalyst G was a Cr/silica containing 1 wt. % Cr, and having an average particle size of 100 um, a BET surface area of 300 m$^2$/g, and a pore volume of 1.3 mL/g. The catalyst was calcined in air at 750° C. for 3 hr to form the chromium (VI)/silica catalyst.

Catalyst H was Catalyst G after reduction in CO at 350° C. for 30 min to form the chromium (II)/silica catalyst.

Catalyst I was a silica-titania-chromia tergel containing 1 wt. % Cr and 4.8% wt. % Ti, having an average particle size of 100 um, a BET surface area of 550 m$^2$/g, and a pore volume of 2.5 mL/g. The catalyst was calcined in air at 850° C. for 3 hr.

Catalyst J was the silica of Catalyst B, impregnated with chromium acetate to 0.5 wt. % Cr, calcined in air at 750° C. for 3 hr, and then reduced in CO at 350° C. for 30 min to form the form the chromium (II)/silica catalyst.

Catalyst K was a silica-coated alumina (Siral 40 HPV, 40 wt. % SiO$_2$), having an average particle size of 25 um, a BET surface area of 450 m$^2$/g, and a pore volume of 1.4 mL/g. The catalyst was calcined in air at 750° C. for 3 hr, followed by CO reduction at 350° C. for 30 min and N$_2$ flush for 30 min at 350° C. to form the chromium (II)/silica-coated alumina catalyst.

Catalyst L was a Cr/silica-titania cogel catalyst containing 1 wt. % Cr and 4 wt. % Ti, with an average particle size of 130 um, a BET surface area of 560 m$^2$/g, and a pore volume of 2.5 mL/g. After calcining in air at 850° C. for 3 hr, the catalyst was contacted with CO at 25° C. for 4 hr in blue light, then flushed with N$_2$ flush for 30 min at 2° C.

Catalyst M was Catalyst L, followed by heating in N$_2$ to 280° C. and flushing for 15 min to remove any volatiles and to return the original chromium (II)/silica-titania catalyst.

BET surface areas can be determined using the BET nitrogen adsorption method of Brunaur et al., *J. Am. Chem. Soc.*, 60, 309 (1938). Total pore volumes can be determined in accordance with Halsey, G. D., *J. Chem. Phys.* (1948), 16, pp. 931. The d50 particle size, or median or average particle size, refers to the particle size for which 50% of the sample has a smaller size and 50% of the sample has a larger size, and can be determined using laser diffraction in accordance with ISO 13320.

Examples 1-22

Alkane Reaction Experiments Using Chromium and Other Catalysts

Table I summarizes Examples 1-22, Table II summarizes the vapor analysis of certain examples in Table I, and Table III summarizes the condensate analysis of certain examples in Table I. From Table I, it apparent that silica (with no chromium, Example 4), silica-titania (with no chromium, Example 6), silica-titania-chromia (hexavalent chromium, Example 16), and chromium (VI)/silica (hexavalent chromium, Examples 13-14) do not convert the alkane reactant into lower or higher molecular weight hydrocarbons. Unexpectedly, supported chromium (II) catalysts using silica (Example 17), silica-coated alumina (Example 20), and silica-titania (Examples 18-19, among others) readily converted the alkane reactant into a variety of lower and higher molecular weight hydrocarbons.

In Example 21, a chromium (VI)/silica-titania was light reduced at 25° C. and then exposed to isopentane vapor at room temperature. No alkane was converted. The same catalyst, in Example 22, was heated in nitrogen to 250° C., and then it readily converted the alkane reactant. While not wishing to be bound by the following theory, it is believed that the nitrogen heating step may have removed residual CO$_2$ ligands from the catalyst, which allows the reaction to proceed. This also may explain why Cr(VI) catalysts did not perform, because they too have ligands left behind, that are not as easily removed.

Table II summarizes the analysis of the vapor product when the alkane reactant was either isopentane or ethane. For the isopentane examples, the conversion in the vapor product ranged from 10 to 60 vol %, and the reaction produced a range of C$_1$-C$_4$ products, as well as a significant amount of hydrogen. For the ethane examples, the conversion was lower, which is consistent with its lower reactivity in general, and the reaction produced mainly methane and propane. For Example 20, two different sampling bags (20-a, 20-b) were taken during this experiment, the first generally capturing the results from the first half of the experiment, and the second generally capturing the second half.

Table III summarizes the analysis of the condensate product when the alkane reactant was either isopentane or n-pentane. A representative listing of the compounds found in the condensate product is presented; not all compounds are listed (or identified) for each example. Referring to Example 1, the products formed indicate that bond-breaking, bond-forming, and re-arrangement reactions have taken place; various alkanes and alkenes were formed, some higher in molecular weight (or carbon number) than pentane, and some lower. Example 3 demonstrates that isopentane is more reactive and formed aromatics in addition to alkanes and alkenes. Examples 17 and 20 illustrate some of the products formed with a different catalyst support from that used in Examples 1 and 3. Examples 18-19 illustrate some of the products formed when the reaction is performed at room temperature, which are generally less than that of Example 1 (elevated temperature).

Also included in Table III is an estimated conversion of the alkane reactant, based solely on condensate/liquid product stream, and was determined by total area of all the products (excluding the reactant) divided by the total area in the GC-MS analysis (including the reactant). Unexpectedly, several examples demonstrated conversion values in the 10-35% range. Nonetheless, as one of skill in the art would readily recognize, the single-pass reactant conversion can be improved or increased using a variety of operational variables, such as pressure, temperature, catalyst type, and flow rate/WHSV, among other variables.

TABLE I

Summary of Examples 1-22.

| Example | Catalyst | Reactant, Conditions | Condensate Analysis | Vapor Analysis |
|---|---|---|---|---|
| 1 | A | n-Pentane, 250° C. | *Higher hydrocarbons | Not analyzed |
| 2 | A | n-Pentane + CO, 250° C. | Nothing | Not analyzed |
| 3 | A | i-Pentane, 300° C. | *Higher hydrocarbons | *C1-C5, and H2 |
| 4 | B | n-Pentane, 250° C. | Nothing | Nothing |
| 5 | C | n-Pentane, 250° C. | Nothing | 0.15% H2, nothing else |
| 6 | D | n-Pentane, 250° C. | Nothing | Nothing |
| 7 | F | n-Pentane, 250° C. | C4 & C6 | Nothing |
| 8 | A | Methane, 300-350° C. | Nothing | Nothing |
| 9 | A | Methane, 500° C. | Nothing | Nothing |
| 10 | A | Ethane, 300° C. | No condensate | *C1-C4, and H2 |
| 11 | A | Ethane, 200° C. | No condensate | *C1-C3 |
| 12 | A | Ethane, 100° C. | No condensate | *C1-C3 |
| 13 | G | i-Pentane, 200° C. | Nothing | Nothing |
| 14 | G | i-Pentane, 300° C. | Nothing | Nothing |
| 15 | H | i-Pentane, 200° C. | Nothing | Trace of C2 |
| 16 | I | i-Pentane, 300° C. | Nothing | Nothing |
| 17 | J | i-Pentane, 350° C. | *C3-C12 mostly | *C1-C5, and H2 |
| 18 | A | n-Pentane, 25° C. | *Higher hydrocarbons | Not analyzed |
| 19 | A | n-Pentane, 25° C. | *Higher hydrocarbons | Not analyzed |
| 20 | K | i-Pentane, 300° C. | *C4-C10 mostly | *C1-C5, and H2 |
| 21 | L | i-Pentane, 25° C. | Nothing | Nothing |
| 22 | M | i-Pentane, 280° C. | *C3-C7 mostly | *C1-C5, and H2 |

*Further information in Table II (vapor) and Table III (condensate).

TABLE II

Summary of Vapor Analysis (vol %).

| Example | 17 | 3 | 10 | 11 | 12 | 20-a | 20-b | 22 |
|---|---|---|---|---|---|---|---|---|
| Hydrogen | 17.65% | 25.99% | 0.27% | 0.00% | 0.00% | 19.49% | 17.41% | 6.02% |
| Methane | 3.32% | 11.32% | 0.57% | 1.31% | 1.31% | 4.18% | 1.57% | 1.86% |
| Ethylene | 2.53% | 1.36% | 0.02% | 0.00% | 0.00% | 0.14% | 0.19% | 0.44% |
| Ethane | 1.18% | 8.11% | 98.82% | 98.56% | 98.56% | 2.91% | 0.82% | 0.33% |
| Propylene | 4.88% | 1.91% | 0.00% | 0.00% | 0.00% | 0.23% | 0.40% | 0.91% |
| Propane | 0.46% | 6.86% | 0.31% | 0.14% | 0.13% | 1.95% | 0.60% | 0.25% |
| Isobutane | 0.16% | 0.84% | 0.00% | 0.00% | 0.00% | 0.43% | 0.17% | 0.03% |
| Butane | 0.06% | 0.56% | 0.01% | 0.00% | 0.00% | 0.82% | 0.29% | 0.00% |
| Isopentane | 45.78% | 42.00% | 0.00% | 0.00% | 0.00% | 68.91% | 77.45% | 89.54% |
| Total C4 | 3.66% | 2.35% | 0.02% | 0.00% | 0.00% | 1.45% | 0.84% | 0.55% |
| Total C5 | 45.94% | 42.10% | 0.00% | 0.00% | 0.00% | 69.65% | 78.17% | 89.65% |
| Conversion | 54.22% | 58.00% | 1.18% | 1.44% | 1.44% | 31.09% | 22.55% | 10.46% |

TABLE III

Summary of Condensate Analysis.

| Example 1 | Example 3 | Example 17 | Example 20 | Example 22 | Example 18 | Example 19 |
|---|---|---|---|---|---|---|
| ~13% conversion | ~34% conversion | ~28% conversion | ~21% conversion | ~10% conversion | ~1% conversion | ~1% conversion |
| Carbon monoxide | propane | propane | $C_4H_8$ | propylene | n-pentane | n-pentane |
| propane, butanol or butanal | 2-butene | $C_4H_8$ | isopentane | $C_4H_8$ | benzene | benzene |

TABLE III-continued

Summary of Condensate Analysis.

| Example 1 | Example 3 | Example 17 | Example 20 | Example 22 | Example 18 | Example 19 |
|---|---|---|---|---|---|---|
| ~13% conversion | ~34% conversion | ~28% conversion | ~21% conversion | ~10% conversion | ~1% conversion | ~1% conversion |
| n-butane | isopentane | isopentane | $C_6H_{14}$ | isopentane | $C_{21}H_{44}$ or $C_{19}H_{40}$ | $C_6H_8O$ |
| n-pentane | $C_6H_{14}O$ | $C_6H_{12}$ | $C_6H_{12}$ | $C_6H_{12}$ | $C_{14}H_{22}O$ | $C_{12}H_{24}$ |
| 2-methyl-pentane | $C_6H_{14}$ | $C_6H_{10}$ | $C_7H_{16}$ | $C_7H_{14}$ | $C_{18}H_{30}$ | $C_{16}H_{32}$ |
| 3-methyl-pentane | $C_6H_{12}$ | benzene | $C_7H_{14}$ | | $C_{17}H_{36}$ | $C_{12}H_{16}$ |
| 1-hexene | n-hexane | $C_7H_{16}$ | $C_6H_{10}O$ | | $C_{12}H_{16}$ | $C_{14}H_{12}O$ |
| n-hexane | benzene | $C_7H_{14}$ | toluene | | $C_{20}H_{52}$ | $C_{18}H_{30}$ |
| 1-butene-3,3-dimethyl | $C_7H_{14}$ | $C_{12}H_{24}$ | $C_9H_{18}$ | | $C_{23}H_{48}$ | $C_{18}H_{30}O$ |
| 2-pentene-3-methyl | $C_7H_{16}$ | $C_8H_{16}$ | $C_{10}H_{20}$ | | $C_{20}H_{24}O_2$ | $C_{19}H_{40}$ |
| cyclohexane | $C_8H_{16}$ | $C_7H_{12}$ | $C_9H_{18}$ | | $C_{17}H_{36}$ or $C_{27}H_{56}$ | $C_{21}H_{44}$ |
| $C_6H_{12}$ | $C_7H_{12}$ (4,4 dimethyl cyclopentene) | toluene | | | phthalate | $C_{26}H_{54}$ |
| $C_7H_{16}$ | $C_8H_{16}$ | $C_9H_{18}$ | | | $C_{26}H_{52}$ | $C_{19}H_{40}$ |
| n-heptane | toluene | ethylbenzene | | | | $C_{26}H_{54}$ |
| $C_7H_{14}$ | $C_8H_{14}$ | p-xylene | | | | |
| $C_8H_{18}$ (dimethyl hexane isomers) | $C_{10}H_{20}$ | $C_{12}H_{24}$ | | | | |
| $C_8H_{18}$ (methyl heptane isomers) | ethylbenzene | | | | | |
| $C_{10}H_{18}$ | m-xylene | | | | | |
| $C_{12}H_{24}$ | p-xylene | | | | | |
| $C_{18}H_{30}$ | $C_{10}H_{18}$ | | | | | |
| $C_{18}H_{30}O$ | $C_{10}H_{16}$ | | | | | |
| $C_{18}H_{30}O_2$ | mesitylene | | | | | |
| Various $C_{20}$ to $C_{30}$ compounds | $C_{12}H_{24}$ | | | | | |

Examples 23-29

Examples 23-29 were performed to determine the extent of reduction of the hexavalent chromium and the average valence after reduction in a representative supported chromium catalyst. Table IV summarizes the results. Example 29 was a chromium/silica-titania catalyst containing approximately 0.8 wt. % chromium and 7 wt. % titania, and having a BET surface area of 530 m²/g, a pore volume of 2.6 mL/g, and an average particle size of 130 um, which was calcined in dry air at 850° C. for 3 hr to convert chromium to the hexavalent oxidation state (orange). This converted over 86 wt. % of the chromium into the hexavalent state. For Examples 23-24, approximate 2 g samples of the catalyst of Example 29 were separately charged to a glass reaction vessel and 0.5 mL of liquid isopentane was charged to the vessel. For Examples 25-26, about 1.5 atm of gaseous ethane was charged to the glass bottle. Then, the bottle was placed in a light-proof box under blue fluorescent light (approximately 2 times the intensity expected from sunlight), and the bottle was continuously rotated so that all of the catalyst was exposed to the light for 24 hr. The final catalyst color is noted in Table IV. Afterward, into the bottle, along with the catalyst, was introduced about 20 mL of a solution of 2 M $H_2SO_4$. To this was added 5 drops of ferroin Fe(+3) indicator. This usually turned a blue-green color indicating the presence of Fe(III) ions. Next, the solution was titrated to the ferroin endpoint (red color) using a solution of ferrous ammonium sulfate, which had been previously calibrated by reaction with a standardized 0.1 M sodium dichromate solution. When the solution turned red, the end point was signaled, and the titrant volume was recorded, to calculate the oxidation capacity of the catalyst, expressed as wt. % Cr(VI) and as percent reduced, that is, the percent of the original Cr(VI) oxidative power that has been removed by the reduction treatment. The average valence was also computed by multiplying the percent reduced by +3 and subtracting that number from +6.

Of course, this treatment gives only an average oxidation state. Note that although Table IV lists the oxidative power measured as wt. % Cr(VI), in reality all of the chromium could be present in lower valence states, such as Cr(IV) or Cr(V). Thus, the Cr(VI) value in Table IV only lists the maximum amount of Cr(VI) that could be present. More likely, the reduced catalysts have a combination of several valence states that produce the measured oxidative power. Note that some of the reduced chromium, and particularly those catalysts reduced with CO, may be in the divalent state, which would not have been detected in this test, which stops in the trivalent state.

Example 29 demonstrates that the air-calcined chromium catalyst contained substantially most of its chromium (0.69/0.80=86 wt. %) present as Cr(VI), and it is this Cr(VI) amount that is being reduced in the light treatment. Therefore, this amount of Cr(VI) serves as the starting amount, which had an average valence of +6, and which serves as a reference, to which the reduced catalysts are then compared. Examples 23-24 were reduced chromium catalysts with an average valence of approximately +3.3, with no more than 0.06 wt. % Cr(VI), and with less than 10 wt. % of the starting hexavalent chromium still remaining in the hexavalent oxidation state. Examples 25-26 were reduced chromium catalysts with an average valence of approximately +4.1, with no more than 0.26 wt. % Cr(VI), and with less than 40 wt. % of the chromium in the hexavalent oxidation state. For Examples 27-28, the catalyst was reduced in CO with either blue light or elevated temperature, resulting in no oxidative power being measured (0 wt. % Cr(VI) in the table). Thus, the average valence must be no more than +3. But the catalyst that was CO-reduced by conventional means (Example 28) is known to have a valence of mostly Cr(II), which is not detected in this test. Accordingly, Examples 27 and 28 are listed as less than or equal to +3. Notably, this test cannot distinguish between Cr(II) and Cr(III) species, but there was no measurable amount of hexavalent chromium in Examples 27-28.

TABLE IV

Examples 23-29

| Example | Reductant | Treatment | Color | Catalyst (g) | Cr (VI) (wt. %) | Reduced (wt. %) | Average Valence |
|---|---|---|---|---|---|---|---|
| 23 | isopentane | Blue light 24 hr | blue | 2.05 | 0.06 | 90.8 | 3.28 |
| 24 | isopentane | Blue light 24 hr | blue | 2.08 | 0.06 | 90.9 | 3.27 |
| 25 | ethane | Blue light 24 hr | olive green | 2.14 | 0.26 | 62.3 | 4.13 |
| 26 | ethane | Blue light 24 hr | olive green | 2.30 | 0.26 | 61.9 | 4.14 |
| 27 | CO | Blue light 2 hr | blue green | 2.33 | 0.00 | 100 | ≤3 |
| 28 | CO | CO reduction 30 min-350° C. | blue | 2.52 | 0.00 | 100 | ≤3 |
| 29 | None | None | orange | — | 0.69 | 0 | 6.00 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for cracking an alkane reactant to form a lower aliphatic hydrocarbon product, the process comprising:
contacting the alkane reactant with a supported chromium (II) catalyst to form the lower aliphatic hydrocarbon product, wherein the lower aliphatic hydrocarbon product has a molecular weight less than that of the alkane reactant.

Aspect 2. The process defined in aspect 1, wherein the alkane reactant comprises a $C_n$ alkane compound, and the lower aliphatic hydrocarbon product comprises a $(C_{n-1})-$ aliphatic hydrocarbon compound.

Aspect 3. The process defined in aspect 1, wherein the alkane reactant comprises a $C_n$ alkane compound, and the lower aliphatic hydrocarbon product comprises a mixture of $(C_{n-1})-$ saturated or unsaturated, cyclic, linear, or branched, aliphatic hydrocarbon compounds.

Aspect 4. The process defined in aspect 1, wherein the alkane reactant comprises a $C_n$ alkane compound, and the lower aliphatic hydrocarbon product comprises a $(C_{n-1})-$ internal alkene, 1-alkene, or a combination thereof.

Aspect 5. The process defined in aspect 1, wherein the alkane reactant comprises a $C_n$ alkane compound, and the lower aliphatic hydrocarbon product comprises a $(C_{n-1})-$ linear alkane, branched alkane, or a combination thereof.

Aspect 6. The process defined in any one of the preceding aspects, wherein contacting the alkane reactant with the supported chromium (II) catalyst forms the lower aliphatic hydrocarbon product and $H_2$.

Aspect 7. The process defined in any one of the preceding aspects, wherein contacting the alkane reactant with the supported chromium (II) catalyst forms the lower aliphatic hydrocarbon product and an isomer of the alkane reactant and/or an aromatic compound (e.g., benzene or toluene).

Aspect 8. A process for converting an alkane reactant into a higher aliphatic hydrocarbon product, the process comprising: contacting the alkane reactant with a supported chromium (II) catalyst to form the higher aliphatic hydrocarbon product, wherein the higher aliphatic hydrocarbon product has a molecular weight greater than that of the alkane reactant.

Aspect 9. The process defined in aspect 8, wherein the alkane reactant comprises a $C_n$ alkane compound, and the higher aliphatic hydrocarbon product comprises a $(C_{n+1})+$ aliphatic hydrocarbon compound.

Aspect 10. The process defined in aspect 8, wherein the alkane reactant comprises a $C_n$ alkane compound, and the higher aliphatic hydrocarbon product comprises a mixture of $(C_{n+1})+$ saturated or unsaturated, cyclic, linear, or branched, aliphatic hydrocarbon compounds.

Aspect 11. The process defined in aspect 8, wherein the alkane reactant comprises a $C_n$ alkane compound, and the higher aliphatic hydrocarbon product comprises a $(C_{n-1})+$ internal alkene, 1-alkene, or a combination thereof.

Aspect 12. The process defined in aspect 8, wherein the alkane reactant comprises a $C_n$ alkane compound, and the higher aliphatic hydrocarbon product comprises a $(C_{n+1})+$ linear alkane, branched alkane, or a combination thereof.

Aspect 13. The process defined in any one of aspects 8-12, wherein contacting the alkane reactant with the supported chromium (II) catalyst forms the higher aliphatic hydrocarbon product and $H_2$.

Aspect 14. The process defined in any one of aspects 8-13, wherein contacting the alkane reactant with the supported chromium (II) catalyst forms the higher aliphatic hydrocarbon product and an isomer of the alkane reactant and/or an aromatic compound (e.g., benzene or toluene).

Aspect 15. The process defined in any one of the preceding aspects, wherein n is any suitable integer or an integer in any range disclosed herein, e.g., from 1 to 36, from 1 to 12, from 2 to 18, or from 2 to 8.

Aspect 16. The process defined in any one of aspects 1-15, wherein the alkane reactant is a cyclic alkane.

Aspect 17. The process defined in any one of aspects 1-15, wherein the alkane reactant is a linear alkane.

Aspect 18. The process defined in any one of aspects 1-15, wherein the alkane reactant is a branched alkane.

Aspect 19. The process defined in any one of aspects 1-15, wherein the alkane reactant comprises any suitable carbon number alkane compound or any carbon number alkane compound disclosed herein, e.g., a $C_1$ to $C_{36}$ alkane compound, a $C_1$ to $C_{12}$ alkane compound, a $C_2$ to $C_{18}$ alkane compound, or a $C_2$ to $C_8$ alkane compound.

Aspect 20. The process defined in any one of aspects 1-15, wherein the alkane reactant comprises any suitable mixture of alkane compounds or any mixture of alkane compounds disclosed herein, e.g., a mixture of $C_1$ to $C_4$ alkane compounds, a mixture of $C_2$ to $C_6$ alkane compounds, a mixture of $C_6$ to $C_8$ alkane compounds, or a mixture of $C_{10}$ to $C_{14}$ alkane compounds.

Aspect 21. The process defined in any one of aspects 1-15, wherein the alkane reactant comprises methane, ethane, propane, butane (e.g., n-butane or isobutane), pentane (e.g., n-pentane, neopentane, or isopentane), hexane, heptane, octane, nonane, decane, undecane, dodecane, tridecane, tetradecane, pentadecane, hexadecane, heptadecane, octadecane, or any combination thereof.

Aspect 22. The process defined in any one of aspects 1-15, wherein the alkane reactant comprises ethane, propane, n-butane, isobutane, n-pentane, neopentane, isopentane, n-hexane, n-heptane, n-octane, n-decane, n-dodecane, or any combination thereof; or the alkane reactant comprises methane, ethane, propane, butane (e.g., n-butane or isobutane), or any combination thereof.

Aspect 23. The process defined in any one of the preceding aspects, wherein the supported chromium (II) catalyst comprises any suitable amount of chromium or an amount in any range disclosed herein, e.g., from about 0.01 to about 50 wt. %, from about 0.01 to about 10 wt. %, from about 0.05 to about 15 wt. %, from about 0.1 to about 15 wt. %, from about 0.2 to about 10 wt. %, from about 0.1 to about 5 wt. %, from about 0.5 to about 30 wt. %, or from about 0.5 to about 2.5 wt. % of chromium, based on the weight of the supported chromium (II) catalyst.

Aspect 24. The process defined in any one of the preceding aspects, wherein the supported chromium (II) catalyst comprises any suitable amount of chromium (II) or an amount in any range disclosed herein, e.g., from about 0.01 to about 50 wt. %, from about 0.01 to about 10 wt. %, from about 0.05 to about 15 wt. %, from about 0.1 to about 15 wt. %, from about 0.2 to about 10 wt. %, from about 0.1 to about 5 wt. %, from about 0.5 to about 30 wt. %, or from about 0.5 to about 2.5 wt. % of chromium (II), based on the weight of the supported chromium (II) catalyst.

Aspect 25. The process defined in any one of the preceding aspects, wherein the supported chromium (II) catalyst comprises at least about 20 wt. %, at least about 50 wt. %, at least about 75 wt. %, at least about 85 wt. %, at least about 90 wt. %, or at least about 95 wt. % of chromium (II), based on the total amount of chromium, and/or the supported chromium (II) catalyst comprises (from 0 wt. %, from about 0.5 wt. %, from about 1 wt. %, or from about 2 wt. %) to less than or equal to about 50 wt. %, less than or equal to about 35 wt. %, less than or equal to about 20 wt. %, or less than or equal to about 10 wt. % of chromium (VI), based on the total amount of chromium.

Aspect 26. The process defined in any one of the preceding aspects, wherein the chromium in the supported chromium (II) catalyst has an average valence of less than or equal to 3.5, less than or equal to 3.25, or less than or equal to 3.

Aspect 27. The process defined in any one of aspects 1-26, wherein the supported chromium (II) catalyst comprises any suitable solid oxide or any solid oxide disclosed herein, e.g., silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, alumina borate, silica-boria, aluminophosphate-silica, titania-zirconia, or any combination thereof.

Aspect 28. The process defined in any one of aspects 1-26, wherein the supported chromium (II) catalyst comprises silica, silica-alumina, silica-coated alumina, silica-titania, silica-titania-magnesia, silica-zirconia, silica-magnesia, silica-boria, aluminophosphate-silica, alumina, alumina borate, or any combination thereof.

Aspect 29. The process defined in any one of aspects 1-26, wherein the supported chromium (II) catalyst comprises a chemically-treated solid oxide comprising a solid oxide (e.g., as in aspect 27 or 28) treated with an electron-withdrawing anion.

Aspect 30. The process defined in aspect 29, wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, or any combination thereof.

Aspect 31. The process defined in aspect 29 or 30, wherein the chemically-treated solid oxide contains from about 1 to about 30 wt. %, from about 2 to about 20 wt. %, from about 2 to about 15 wt. %, from about 3 to about 12 wt. %, or from 4 to 10 wt. %, of the electron-withdrawing anion, based on the total weight of the chemically-treated solid oxide.

Aspect 32. The process defined in any one of aspects 1-26, wherein the supported chromium (II) catalyst comprises a chemically-treated solid oxide comprising fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 33. The process defined in any one of aspects 1-26, wherein the supported chromium (II) catalyst comprises chromium (II)/silica, chromium (II)/silica-titania, chromium (II)/silica-titania-magnesia, chromium (II)/silica-alumina, chromium (II)/silica-coated alumina, chromium (II)/aluminophosphate, chromium (II)/alumina, chromium (II)/alumina borate, or any combination thereof.

Aspect 34. The process defined in any one of aspects 1-26, wherein the supported chromium (II) catalyst comprises chromium (II)/silica-titania, and the supported chromium (II) catalyst comprises any suitable amount of titanium or an amount in any range disclosed herein, e.g., from about 0.1 to about 20 wt. %, from about 0.5 to about 15 wt. %, from about 1 to about 10 wt. %, or from about 1 to about 6 wt. %, based on the weight of the supported chromium (II) catalyst.

Aspect 35. The process defined in any one of aspects 1-26, wherein the supported chromium (II) catalyst comprises chromium (II)/sulfated alumina, chromium (II)/fluorided alumina, chromium (II)/fluorided silica-alumina, chromium (II)/fluorided silica-coated alumina, or any combination thereof.

Aspect 36. The process defined in any one of aspects 1-26, wherein the supported chromium (II) catalyst comprises a zeolite.

Aspect 37. The process defined in aspect 36, wherein the zeolite comprises a medium pore zeolite, a large pore zeolite, or a combination thereof.

Aspect 38. The process defined in aspect 36, wherein the zeolite comprises a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, and a Ferrierite framework type zeolite, or a combination thereof.

Aspect 39. The process defined in aspect 36, wherein the zeolite comprises an L-zeolite, a Y-zeolite, a mordenite, an omega zeolite, and/or a beta zeolite.

Aspect 40. The process defined in any one of aspects 36-39, wherein the supported chromium (II) catalyst comprises a zeolite and any suitable amount of binder or an amount in any range disclosed herein, e.g., from about 3 wt. % to about 35 wt. %, or from about 5 wt. % to about 30 wt. % binder, based on the total weight of the supported chromium (II) catalyst.

Aspect 41. The process defined in any one of the preceding aspects, wherein the supported chromium (II) catalyst has any suitable pore volume (total) or a pore volume (total) in any range disclosed herein, e.g., from about 0.1 to about 5 mL/g, from about 0.15 to about 5 mL/g, from about 0.1 to about 3 mL/g, or from about 0.15 to about 2 mL/g.

Aspect 42. The process defined in any one of the preceding aspects, wherein the supported chromium (II) catalyst has any suitable BET surface area or a BET surface area in any range disclosed herein, e.g., from about 50 to about 2000 $m^2/g$, from about 50 to about 700 $m^2/g$, from about 50 to about 400 $m^2/g$, from about 100 to about 1200 $m^2/g$, or from about 150 to about 525 $m^2/g$.

Aspect 43. The process defined in any one of the preceding aspects, wherein the supported chromium (II) catalyst is in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagonwheel, monolith, or any combination thereof.

Aspect 44. The process defined in any one aspects 1-43, wherein the supported chromium (II) catalyst has any suitable average (d50) particle size or an average (d50) particle size in any range disclosed herein, e.g., from about 10 to about 500 microns, from about 25 to about 250 microns, or from about 20 to about 100 microns.

Aspect 45. The process defined in any one aspects 1-43, wherein the supported chromium (II) catalyst comprises pellets or beads having any suitable average size or an average size in any range disclosed herein, e.g., from about 1/16 inch to about 1/2 inch, or from about 1/8 inch to about 1/4 inch.

Aspect 46. The process defined in any one of the preceding aspects, wherein the higher aliphatic hydrocarbon product (or the lower aliphatic hydrocarbon product) is formed at a temperature from about 0° C. to about 800° C.

Aspect 47. The process defined in any one of the preceding aspects, wherein the higher aliphatic hydrocarbon product (or the lower aliphatic hydrocarbon product) is formed at a temperature from about 20° C. to about 300° C., from about 20° C. to about 250° C., from about 100° C. to about 200° C., or from about 300° C. to about 600° C.

Aspect 48. The process defined in any one of the preceding aspects, wherein the weight ratio of the alkane reactant to chromium (of the supported chromium (II) catalyst) is in any suitable range or any range disclosed herein, e.g., from about 5:1 to about 1000:1, from about 10:1 to about 500:1, or from about 15:1 to about 150:1.

Aspect 49. The process defined in any one of aspects 1-48, wherein the process comprises contacting the alkane reactant in a gas phase with the supported chromium (II) catalyst.

Aspect 50. The process defined in any one of aspects 1-48, wherein the process comprises contacting the alkane reactant in a liquid phase with the supported chromium (II) catalyst.

Aspect 51. The process defined in any one of aspects 1-48, wherein the process comprises a slurry (e.g., a loop slurry) of the supported chromium (II) catalyst in the alkane reactant.

Aspect 52. The process defined in any one of aspects 1-48, wherein the process comprises contacting the alkane reactant with a fluidized bed of the supported chromium (II) catalyst.

Aspect 53. The process defined in any one of aspects 1-48, wherein the process comprises contacting the alkane reactant (e.g., in a gas phase or in a liquid phase) with a fixed bed of the supported chromium (II) catalyst.

Aspect 54. The process defined in any one of the preceding aspects, wherein the step of contacting the alkane reactant with the supported chromium (II) catalyst is conducted at any suitable WHSV or a WHSV in any range disclosed herein, e.g., from about 0.01 $hr^{-1}$ to about 500 $hr^{-1}$, or from about 0.1 $hr^{-1}$ to about 10 $hr^{-1}$.

Aspect 55. The process defined in any one of the preceding aspects, wherein the conversion of the alkane reactant (or the yield to the higher aliphatic hydrocarbon product, or the yield to the lower aliphatic hydrocarbon product) is any percent conversion (or yield) disclosed herein, e.g., at least about 2 wt. %, at least about 5 wt. %, at least about 10 wt. %, or at least about 15 wt. % (and up to about 99 wt. %, about 95 wt. %, about 90 wt. %, about 80 wt. %, about 70 wt. %, or about 50 wt. %).

Aspect 56. The process defined in any one of the preceding aspects, wherein the single pass conversion of the alkane reactant (or the single pass yield to the higher aliphatic hydrocarbon product, or the single pass yield to the lower aliphatic hydrocarbon product) is any single pass percent conversion (or single pass yield) disclosed herein, e.g., at least about 2 wt. %, at least about 5 wt. %, at least about 10 wt. %, or at least about 15 wt. % (and up to about 99 wt. %, about 95 wt. %, about 90 wt. %, about 80 wt. %, about 70 wt. %, or about 50 wt. %).

Aspect 57. The process defined in any one of the preceding aspects, further comprising a step of separating at least a portion (and in some cases, all) of the alkane reactant from the higher aliphatic hydrocarbon product (or the lower aliphatic hydrocarbon product) using any suitable technique or any technique disclosed herein, e.g., extraction, filtration, evaporation, distillation, or any combination thereof.

Aspect 58. The process defined in aspect 57, wherein the at least a portion of the alkane reactant is recycled and contacted with the supported chromium (II) catalyst again.

Aspect 59. The process defined in any one of the preceding aspects, wherein the process produces both the lower aliphatic hydrocarbon product and the higher aliphatic hydrocarbon product.

Aspect 60. The process defined in any one of the preceding aspects, wherein the process does not comprise a mineral acid.

Aspect 61. The process defined in any one of the preceding aspects, further comprising a step of regenerating at least a portion (and in some cases, all) of the supported chromium (II) catalyst (after contacting the alkane reactant with the supported chromium (II) catalyst).

Aspect 62. A process comprising:
(i) reducing a supported chromium (VI) catalyst to form the supported chromium (II) catalyst using any suitable technique or any technique disclosed herein, e.g., CO reduction, UV light reduction, elevated temperature reduction, or any combination thereof; and (ii) performing the process defined in any one of the preceding aspects.

We claim:

1. A process for cracking an alkane reactant to form a lower aliphatic hydrocarbon product, the process comprising:
   contacting the alkane reactant with a supported chromium (II) catalyst to form the lower aliphatic hydrocarbon product, wherein the lower aliphatic hydrocarbon product has a molecular weight less than that of the alkane reactant; wherein:
   the alkane reactant comprises a $C_n$ alkane compound;
   the lower aliphatic hydrocarbon product comprises a $(C_{n-1})$- aliphatic hydrocarbon compound;
   n is an integer from 2 to 36; and
   the lower aliphatic hydrocarbon product is formed at a temperature from about 10° C. to about 350° C.

2. The process of claim 1, wherein the alkane reactant comprises ethane, propane, butane, pentane, hexane, heptane, octane, nonane, decane, undecane, dodecane, tridecane, tetradecane, pentadecane, hexadecane, heptadecane, octadecane, or any combination thereof.

3. The process of claim 1, wherein contacting the alkane reactant with the supported chromium (II) catalyst forms the lower aliphatic hydrocarbon product and:
   $H_2$;
   an isomer of the alkane reactant;
   an aromatic compound;
   a higher aliphatic hydrocarbon product, wherein the higher aliphatic hydrocarbon product has a molecular weight greater than that of the alkane reactant; or
   any combination thereof.

4. The process of claim 1, wherein:
   the lower aliphatic hydrocarbon product is formed at a temperature from about 20° C. to about 300° C.; and
   a conversion of the alkane reactant is at least about 10 wt. %.

5. The process of claim 1, wherein:
   the supported chromium (II) catalyst contains from about 0.01 to about 50 wt. % of chromium, based on the weight of the supported chromium (II) catalyst; and
   the supported chromium (II) catalyst contains chromium having an average valence of less than or equal to 3.

6. The process of claim 1, wherein the process comprises contacting the alkane reactant with a fluidized bed of the supported chromium (II) catalyst.

7. The process of claim 1, wherein the process comprises contacting the alkane reactant with a fixed bed of the supported chromium (II) catalyst.

8. The process of claim 1, wherein the supported chromium (II) catalyst contains chromium having an average valence of less than or equal to 3.

9. The process of claim 1, wherein the supported chromium (II) catalyst comprises a solid oxide, a chemically-treated solid oxide, a zeolite, or a combination thereof.

10. The process of claim 1, wherein a conversion of the alkane reactant is at least about 10 wt. %.

11. The process of claim 1, wherein contacting the alkane reactant with the supported chromium (II) catalyst forms the lower aliphatic hydrocarbon product and $H_2$.

12. The process of claim 1, wherein contacting the alkane reactant with the supported chromium (II) catalyst forms the lower aliphatic hydrocarbon product and an isomer of the alkane reactant.

13. The process of claim 1, wherein contacting the alkane reactant with the supported chromium (II) catalyst forms the lower aliphatic hydrocarbon product and an aromatic compound.

14. The process of claim 1, further comprising:
   forming an effluent comprising the lower aliphatic hydrocarbon product; and
   separating at least a portion of the alkane reactant from the effluent, and wherein the at least a portion of the alkane reactant is recycled and contacted with the supported chromium (II) catalyst again.

15. The process of claim 1, further comprising a step of regenerating at least a portion of the supported chromium (II) catalyst.

16. A process for cracking an alkane reactant to form a lower aliphatic hydrocarbon product, the process comprising:
   contacting the alkane reactant with a supported chromium (II) catalyst to form the lower aliphatic hydrocarbon product, wherein the lower aliphatic hydrocarbon product has a molecular weight less than that of the alkane reactant;
   wherein contacting the alkane reactant with the supported chromium (II) catalyst forms the lower aliphatic hydrocarbon product and a higher aliphatic hydrocarbon product, wherein the higher aliphatic hydrocarbon product has a molecular weight greater than that of the alkane reactant.

17. A process for cracking an alkane reactant to form a lower aliphatic hydrocarbon product, the process comprising:
   contacting the alkane reactant with a supported chromium (II) catalyst to form the lower aliphatic hydrocarbon product, wherein the lower aliphatic hydrocarbon product has a molecular weight less than that of the alkane reactant;
   wherein the lower aliphatic hydrocarbon product is formed at a temperature from about 20° C. to about 300° C.

18. The process of claim 17, wherein the alkane reactant comprises a $C_2$ to $C_{18}$ alkane compound.

19. A process for cracking an alkane reactant to form a lower aliphatic hydrocarbon product, the process comprising:
   reducing a supported chromium (VI) catalyst with carbon monoxide to form a supported chromium (II) catalyst; and
   contacting the alkane reactant with the supported chromium (II) catalyst to form the lower aliphatic hydrocarbon product, wherein the lower aliphatic hydrocarbon product has a molecular weight less than that of the alkane reactant.

20. The process of claim 19, wherein the alkane reactant comprises a $C_2$ to $C_{18}$ alkane compound.

* * * * *